United States Patent [19]

Voigt et al.

[11] Patent Number: 4,893,511
[45] Date of Patent: Jan. 16, 1990

[54] METHOD AND APPARATUS FOR DETERMINING CRACKS IN A SHAFT BY MEANS OF AN ULTRASOUND PULSE ECHO

[75] Inventors: Wilhelm Voigt; Ingo Hildmann, both of Berlin, Fed. Rep. of Germany

[73] Assignee: Siemens Aktiengesellschaft, Munich, Fed. Rep. of Germany

[21] Appl. No.: 233,137

[22] Filed: Aug. 17, 1988

[30] Foreign Application Priority Data

Aug. 21, 1987 [DE] Fed. Rep. of Germany ....... 3728369

[51] Int. Cl.$^4$ ............................................ G01N 29/04
[52] U.S. Cl. ........................................ 73/622; 73/634
[58] Field of Search ................... 73/598, 622, 660, 634

[56] References Cited

U.S. PATENT DOCUMENTS 3,934,457 1/1976 Clark et al. .

FOREIGN PATENT DOCUMENTS 1302889 7/1962 France ................................. 73/622
2134255 8/1984 United Kingdom .

OTHER PUBLICATIONS

"Werkstoffprufung mit Ultraschall", Springer Verlag, 5, Auflage, 1986, pp. 176–179, 349 and 382–389.
"Ultrasonic Inspection of Railway Axles" B. R. Byrne et al., *Ultrasonics*, vol. 4 (Jul. 1966), pp. 143–151.
"Ultrasonic Testing of Material" Springer–Verlag, Third Edition, 1983.

*Primary Examiner*—John Chapman
*Assistant Examiner*—Lawrence G. Fess
*Attorney, Agent, or Firm*—Kenyon & Kenyon

[57] ABSTRACT

Method and apparatus for detecting cracks in a shaft by means of an ultrasound pulse echo method. A test hand having an ancillary wedge is coupled to the end face of the shaft for conducting nondestructive testing of the shaft. The test head emits ultrasound pulses of a determined frequency and is moved by means of a mechanical device in front of the end face. The method makes possible reliable and reproducible detection of cracks present at the circumference of long shafts. The test head delivers sound pulses in the range of 4 to 8 MHz and is placed by means of the device at a radial distance from the shaft end face's central axis. The test head is moved in the course of the measurements in three degrees of freedom; along a radius of the shaft, along a circle of the shaft and about the axis of the test head holder. The method and apparatus are employed for testing long turbine shafts in the assembled condition from the end face on the generator side of the shaft.

23 Claims, 4 Drawing Sheets

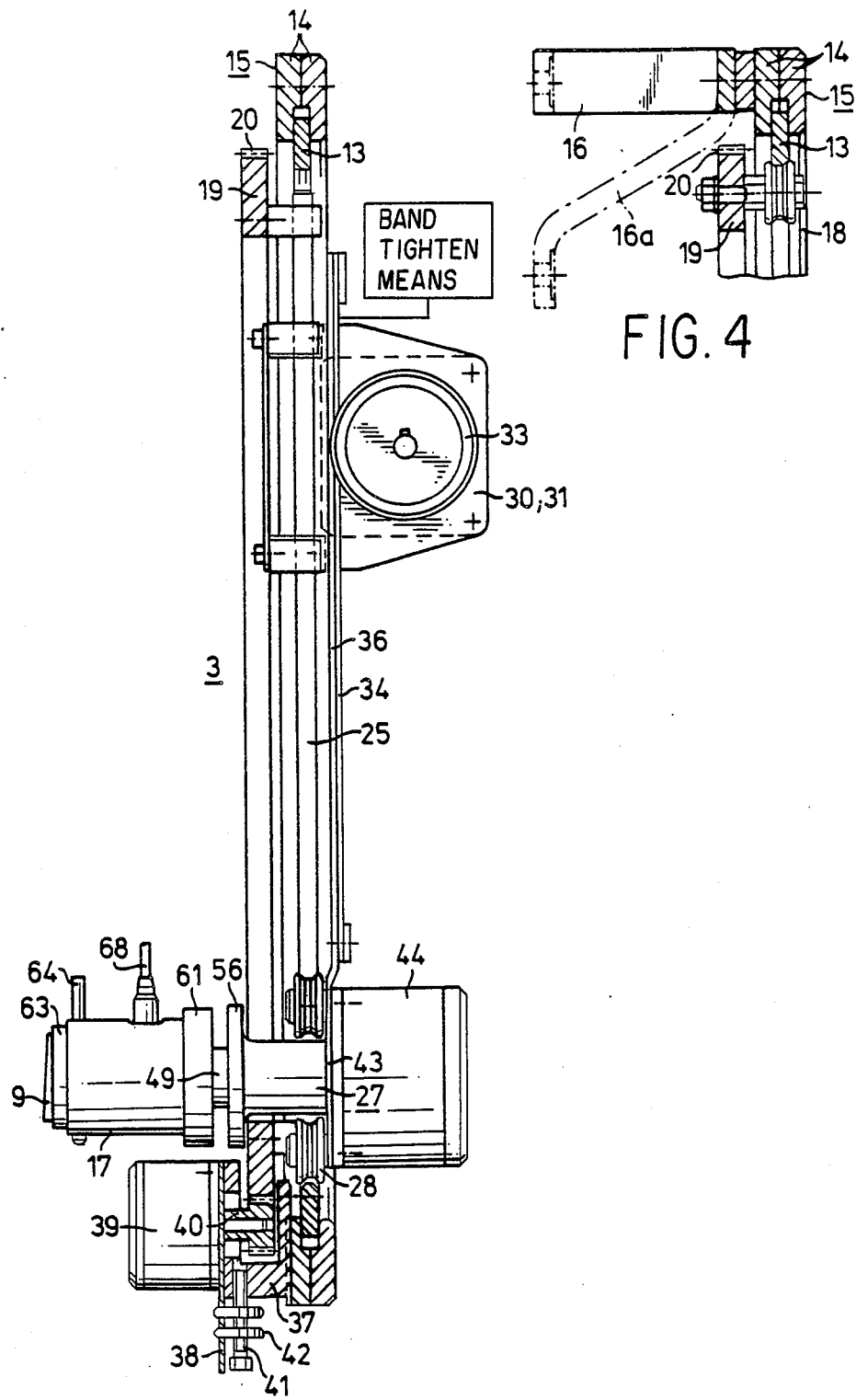

METHOD AND APPARATUS FOR DETERMINING CRACKS IN A SHAFT BY MEANS OF AN ULTRASOUND PULSE ECHO

FIELD OF THE INVENTION

The invention relates to a method and apparatus for detecting cracks in a shaft by means of an ultrasound pulse echo method and, more particularly, to a test head equipped with an ancillary wedge which is coupled to the end face of the shaft and is moved on the shaft by means of a mechanical device. The test head emits ultrasound pulses of a definite frequency and picks up the reflected sound echos with a sound receiver contained in the test head. The results are recorded by an evaluation device.

BACKGROUND OF THE INVENTION

Ultrasound pulse echo methods of the kind described above are known from the text: "Werkstoffpruefung mit Ultraschall", Springerverlag, Fifth Edition, pp. 176–179, 349 and 382–389, by Josef Krautkraemer and Herbert Krautkraemer. It is customary for the known pulse echo methods to utilize transversal as well as longitudinal sound waves with respect to the shaft. Accordingly, for testing shafts, the test head delivering the ultrasound waves having a frequency range of 2 to 5 MHz, is placed adjacent the end face or cylinder face of the shaft and is coupled thereto. Additionally, ancillary wedges are arranged in front of the test head to allow an angular alignment of the test head's sound beam. The choice of the coupling point or the mounting surface for the test head depends upon the geometric nature as well as the material composition of the test piece.

It is known for shorter shafts, such as the axles for a set of railroad wheels, to sonicate the axle shaft from the end face. In the case of longer test pieces, such as turbine shafts, the test heads are guided along the cylinder surface usually with the aid of mechanical devices. To move the test heads along the cylinder surface presupposes that the cylinder surfaces are accessible. A problem arises for long shafts when the cylinder surface is not accessible. An example are wheel discs which have blades that are mounted on a turbine shaft and require shoulders on the shaft for fastening. The coupling of the wheels to the shaft can form starting points for cracks which arise in operation of the shafts. Nondestructive material testing using the pulse echo method along the cylinder surface requires a large and cumbersome number of technical devices as the turbine shaft must first be removed, at least from the stator or housing, for the test. Further, in order to perform a complete test, the wheel discs must be removed as most cracks are located under the wheel discs.

Thus, there is a need to provide a method for detecting cracks in a shaft by means of ultrasound pulse echo methods which permits detecting cracks from the end face of long shafts while the shaft remains in its assembled state and which is reliably reproducible and effected in a simple manner. Such a method should also permit reliable detection of cracks or incipient cracks existing at the shaft circumference. There is also a need for a mechanical device suitable for carrying out such a method.

SUMMARY OF THE INVENTION

A solution to the above problems features a method for detecting cracks in a shaft by means of ultrasound pulse echo methods of the kind described above having a test head which delivers high frequency sound pulses in the range of 4 to 8 MHz. The test head is mounted at on the end face a radial distance from the central axis of the test shaft by means of a mechanical device centered with respect to the central axis. The test head is displaced in the course of the measurement over at least part of the circumference of a circle defined by the radial distance of the test head from the central axis of the test shaft.

By using high frequency ultrasound, a concentrated sound beam is obtained which generates distinct echos when encountering cracks. The high frequency allows cracks to be detected at distances up to several meters. Because the displacement of the test head is uniform and always reproducible as controlled by the mechanical device over a radius or diameter of the shaft and along corresponding circles around the central axis of the shaft, it is therefore possible to scan the entire length of the outside circumference of the shaft from one end face. For this purpose, the state of assembly of the shaft is immaterial as long as there is one end face exposed. It is substantially more simple to expose an end face of the shaft than to disassemble the shaft including the parts arranged thereon.

The accuracy of the method is increased further by providing the test head, located in a test head holder, with an ancillary wedge. The test head and wedge are rotated about the axis of the test head holder. The ancillary wedge slants the sonication of the shaft. This produces a sound beam which can cover a still larger diameter range, i.e. a cone shaped sound beam. In addition, slanted cracks are more clearly picked up by the use of the ancillary wedge and the rotation of the test head.

An apparatus for carrying out the method is designed such that the displacements of the test head along a radius or diameter of the shaft, along a circle about the central axis of the shaft, and about the axis of the test head holder are independent of each other. Accordingly, the apparatus has three degrees of freedom which may be carried out manually or by separate positioning motors.

It is a particular advantage to use the method of the present invention when testing a turbine shaft having an end face coupled to a generator in its assembled state. To accomplish the testing, it is only necessary to disengage the coupling with the generator and to pull the generator shaft forward. Further, it is advantageous to utilize the holes on the end face of the shaft or on the end face of a hub body having coupling pins to serve as a coupling flange arranged on the shaft, for fastening the mechanical device.

In an advantageous embodiment of the invention, the apparatus for carrying out the method comprises a guide ring which is arranged on a support body being adjustably fastened to the test shaft. A second ring is centrally and rotatably supported by the first guide ring and support body. Two tracks are mounted on the second ring and disposed parallel to each other at the same distance from the center of the ring. A slide arrangement is movable lengthwise over the parallel tracks. The slide carries a holder having a test head located therein; the test head, in particular, being provided with the ancillary wedge.

Because the fastening means for the support body having the guide ring is adjustably mounted to the shaft, the diameter of the guide ring is independent of the diameter of the test shaft. The apparatus can therefore be mounted to different shafts, the diameter of which varies over a given range. The guide ring is fastened to the shaft and accurately centered with respect to the central axis of the shaft. It guides the second ring which is rotatably supported therein. Therefore, a first degree of freedom for the motion of the test head along circles around the central axis of the shaft is achieved as the central axis of the shaft corresponds to the center of the rings in the device. The second rotatable ring supports the slide arrangement including the test head. The test head can therefore be moved on the parallel tracks along a radius or diameter of the shaft. The track mounting is designed on one side of the second guide ring so that it is possible to guide the slide arrangement up to the running surface of the guide ring.

To release the longitudinal motion of the slide and test head along the parallel tracks on a radius or diameter of the test shaft, it is advantageous to connect the slide to a band which is looped around a drum rotated by a positioning motor. The band is fastened on the drum and therefore can be wound and unwound. Since the band only transmits tensile forces, a guide track is further provided. The guide track is connected to the slide at one end. The length of the guide track corresponds at least to the desired longitudinal motion for the slide having the ends of the band fastened thereto. The tensile forces exerted by the band due to the rotation of the drum are transmitted to one of the ends of the guide track as tensile or compression forces on the slide. These forces move the slide on the tracks. The conversion of the rotary motion of the drum into straight, reciprocating longitudinal motion is completely free of any play in the system, thus guaranteeing the accurate reproducibility of the test head displacements. It is further advantageous to provide a means for tightening the band to always insure good contact with the drum.

It is advantageous to provide the second rotatable ring with gearing on its circumference to engage the pinion of a second positioning motor. However, in order to allow manual rotation of the second ring, the second positioning motor is advantageously fastened to the support body of the guide ring such that it can be radially moved. The radial movement of the positioning motor allows the pinion to disengage from the external gearing thus leaving the second ring free for simple manual rotation.

DESCRIPTION OF THE DRAWINGS

FIG. 3 is a cross-sectional view along the line III—III of FIG. 2.

FIG. 4 is a cross-sectional view along the line IV-IV of FIG. 2.

DETAILED DESCRIPTION

Turbine shafts in general, especially low-pressure turbine shafts, have a very large length, i.e., greater than 6 m. The shafts are provided with shoulders used to fasten the wheel discs to the shaft. However, in operation of the turbine shafts, cracks have a tendency to form at the shoulders due to the notch effect and the dynamic stresses on the shaft. If the cracks are not discovered in time, they can result in catastrophic fractures of the turbine shafts.

Figure 1:
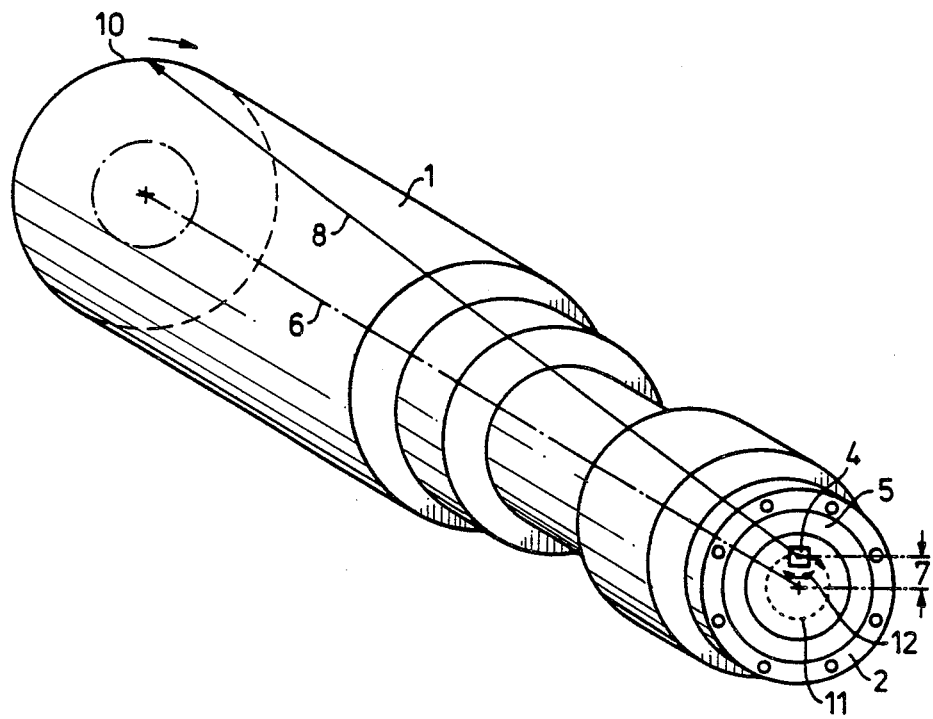
FIG. 1 is a perspective and schematic view of part of a turbine shaft having a test head located at an end face.

Referring to FIG. 1, there is shown a perspective and schematic view of part of a turbine shaft. In order to carry out the method for detecting cracks by means of ultrasound pulse echo methods, it is sufficient for the present invention to have at least one end face 2 freely accessible. Particularly, for turbine shafts, it is preferable to have the end face 2 on the generator side accessible to perform the test. The test head 4 is placed by means of a adjustable mechanical device 3 on the end face 2 as shown in FIGS. 2 through 5. The drill holes 5 in the end face 2 can be utilized for fastening the adjustable mechanical device 3.

Figure 5:
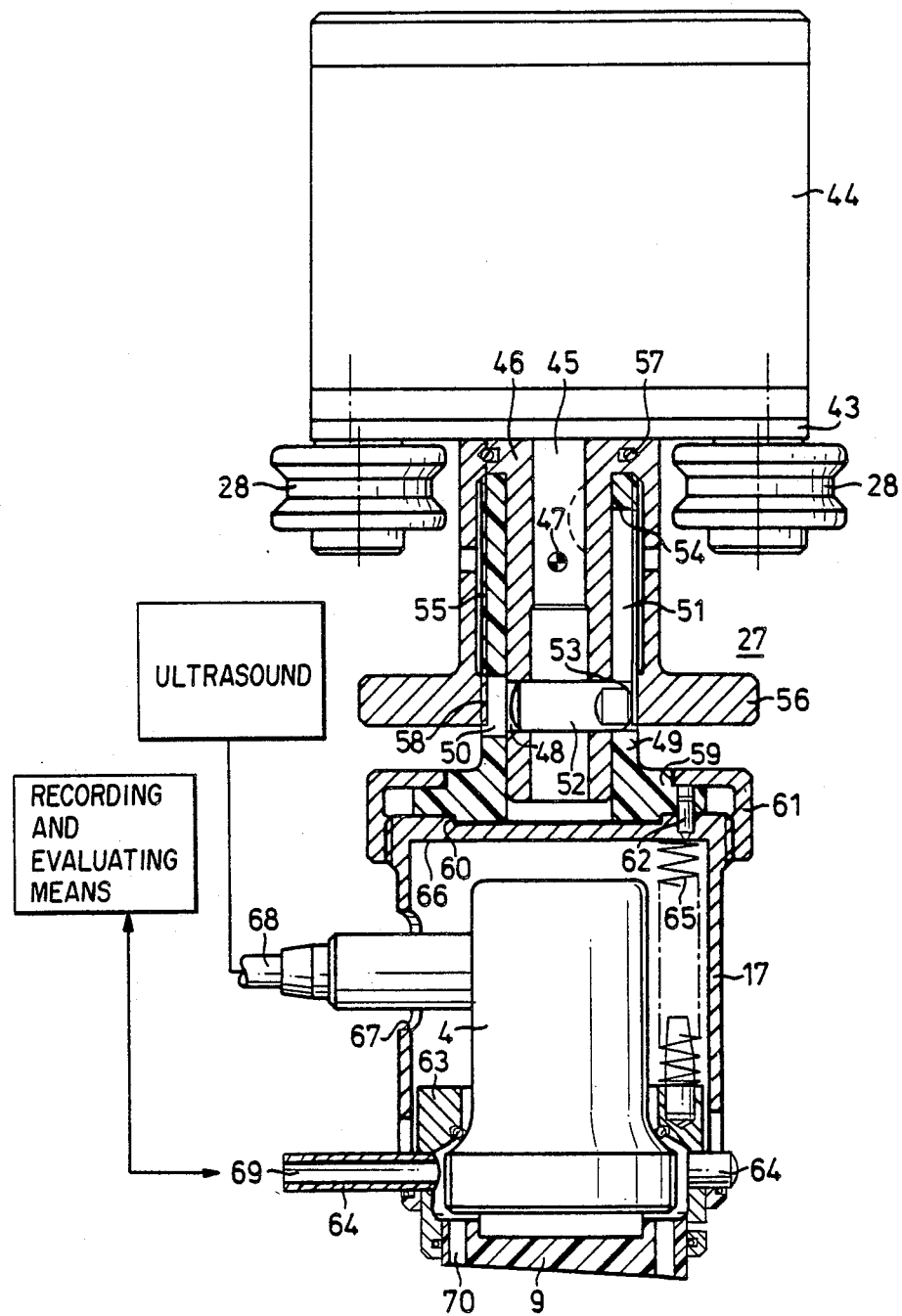
FIG. 5 is a cross-sectional detailed view of the slide arrangement of FIG. 3.

According to the method of the invention, the test head 4 is placed laterally with respect to the central axis 6 of the shaft as indicated by the dashed lines. The test head 4 therefore has a certain radial distance 7 from the central axis 6 of the shaft 1. The test head 4 delivers high frequency ultrasound pulses in the range of 4 to 8 MHz. These pulses form a sound beam 8 as indicated by an arrow in FIG. 1. The sound beam, after travelling a certain length determined by the inclination of the test head to the shaft end face 2 reaches the outside cylinder surface 10 of the turbine shaft 1. Inclination of the test head 4 is obtained through the use of an ancillary wedge 9 as shown in FIGS. 3 and 5. The test head 4 is moved circularly on the end face 2, indicated by dashed circle 11, about the central axis 6. The circular motion allows the outside cylinder surface 10, where most cracks are formed, to be throughly checked. Besides this degree of freedom, the test head 4 can also be rotated about its axis or the axis of the ancillary wedge 9, as indicated by the arrows 12.

Additionally, the test head 4 can be moved along a diameter of the shaft 1 by varying the radial distance 7. The sound beam 8 can therefore cover the outside cylinder surface 10 for turbine shafts having a range of different lengths. This method has the further advantage of excluding from the measurement the central region of the shaft 1 which is adjacent to the central axis 6. This alleviates the detrimental effects that forged parts, such as in turbine shafts, have on the measurements. When the emitted sound beam from the test head 4 encounters a crack in the shaft, at least part of the ultrasound is reflected and bounced back to the end face 2. A sound receiver contained in the test head 4 picks up the echo pulses and feeds them to an evaluating device for recording.

Figure 2:
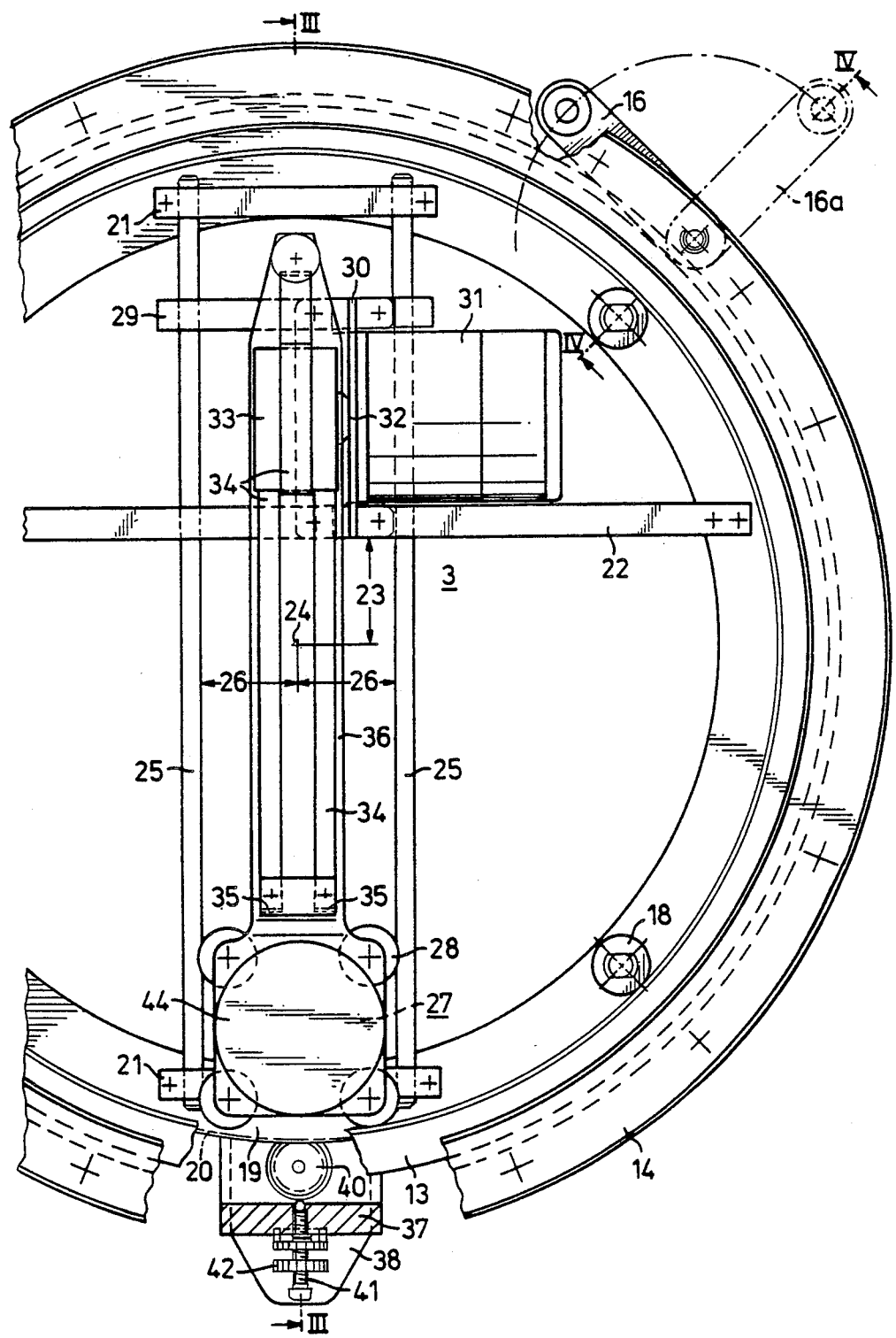
FIG. 2 is a partial cross-sectional top view of an apparatus according to the present invention.

Referring to FIG. 2, the device 3 for manipulating the test head 4 during the measurement contains a guide ring 13 arranged in a support body 15 formed by two clamping rings 14. The support body 15 further comprises adjustable, and in particular, tiltable fastening means 16 which are designed as legs via which the device 3 is fastened to the end face 2 by the holes 5. The fastening means 16 is shown in FIGS. 2 and 4 where fastening means 16a is shown in different positions by the broken lines. The fastening means 16 holds the adjustable mechanical device 3 at a given axial distance in front of the shaft end face 2. The axial distance is chosen large enough so that the test head 4, located with the ancillary wedge 9 in the test head holder 17, can move unimpeded relative to the end face 2 when placed on the end face and coupled thereto.

Because of the adjustable or tiltable nature of the fastening means, both the fastening means 16 and the diameter of the guide ring 13 are independent of the given diameter of the shaft 1. Therefore, the entire device 3 is independent of the given shaft diameter allowing the adjustable mechanical device 3 to be used for different shaft diameters at least to the extent that the sound beam 8 can still reach the outside cylinder surface 10 of the desired length shaft 1. By use of the fastening means 16, the guide ring 13 can always be aligned to have its center coincide exactly with the central axis 6 of the shaft 1.

A second rotatable ring 19 is supported on the inner circumference of the guide ring 13 by means of four rolls 18 located laterally next to the guide ring 13. The second ring 19 is therefore also exactly concentric with respect to the central axis 6 of the shaft 1. The second ring 19 has gearing located on its external circumference.

Fastened on the second ring 19 of the device 3 are several mutually parallel traverses; two short traverses 21 of which are disposed near the outside circumference of the ring 19. A longer traverse 22 is disposed laterally at a distance 23 (shown by arrows) from the center 24 of the device rings 13. The center 24, in the coupled and assembled state of the device 3, is located on the extended central axis of the shaft 1. The traverses 21 and 22 support two mutually parallel tracks 2 aligned perpendicularly thereto. Each track 25 is the same distance 26 from the center 24 of the adjustable mechanical device 3 as shown by arrows in FIG. 2. A lengthwise movable slide 27 is arranged on the tracks 25. The slide arrangement 27 slides and is guided via lateral rolls 28 on the tracks 25. The slide arrangement 27 carries the test head holder 17.

A further traverse 29 is arranged between a short traverse 21 and the long traverse 22 on one side of the center 24. On one side of the traverse 29 is supported a base plate 30 extending parallel to a track 25. A first positioning motor 31 is fastened on the base plate 30. The shaft 32 of the motor 31 extends through the base plate 30 and drives a drum 33. The hub of the drum as well as the shaft 32 of the positioning motor 31 are perpendicular to the tracks 25. The drum 33 serves for winding and unwinding a band 34 of sheet metal which moves the slide 27.

The band 34 is in the form of a tuning fork, i.e. a fork with two tines. The two ends 35 of the band's tine port are connected to both the slide 27 and one end of a guide track 36. The guide track 36 has a length at least corresponding to the desired longitudinal motion of the slide 27. At the other end of the guide track 36, opposite the slide 27, the opposite end of the band is fastened. In between the band's ends, the band is looped around the drum 33. The band's central part, i.e., the transition area from two tines to the single band end, is fixed on the drum 33 (not shown). The winding or unwinding of the band 34 occurs when the drum 33 is rotated by the positioning motor 31. Due to the special form of the band 34, the one-piece end of the band 34 is unimpededly wound and unwound between the two tine-like ends.

The band 34 is in pretensioned contact with the drum 33. Tightening means of a type known to those skilled in the art are provided so that the pretension amount can be subsequently readjusted at any time after extended operation. If the drum 33 is rotated, the band 34 exerts a tensile force on one end of the guide track 36. Depending upon the direction of rotation of the drum 33, a force is transmitted either directly as a tensile force on the slide 27, or as a compression force acting via the other side of the guide track 36. As a result, the slide 27 can be moved in either direction. The conversion of rotary motion to the slide's longitudinal motion, as caused by the positioning motor's 31 rotating drum 33, is completely free of play. Further, the exact motion is therefore reproducible at any time.

Through a suitable design of the short traverse 21, located on the test head side of center 24, the slide 27 can be moved outward so that the test head holder 17 lies directly in front of the inner circumference of the ring 19. Thus, the slide 27 can move over a distance which is larger than the radius of the ring 19. The longitudinally movable slide 27 provides a first degree of freedom for the adjustable mechanical device 3.

The second degree of freedom for the adjustable mechanical device 3 is achieved by rotary motion of the ring 19. The ring 19 can be manually or mechanically released. This is accomplished by using a support shoe 37 having a movable base plate 38 thereon. A second positioning motor 39 is fastened through the base plate 38 to the support body 15 of the guide ring 13. The pinion 40 of the positioning motor 39 normally engages the external gearing 20 of the ring 19 to impart rotation thereto. A fixed screw 41 is provided in the support shoe 37. Attached to the fixed screw is a knurled nut 42 used to adjust the motor position. The nut 42 extends into a slot of the base plate 38 so that the base plate 38 can be shifted radially when the knurled nut 42 is turned. Shifting the base plate 38 also shifts the motor 39 such that the pinion 40 disengages from the external gearing 20. Therefore, the ring 19 no longer encounters resistance from the pinion and can be rotated by hand.

The test head holder 17 including the test head 4 required for carrying out the ultrasound pulse echo method is arranged on the slide 27. The arrangement, as shown in FIG. 5, allows a third degree of freedom, mainly, rotation of the test head 4 about the axis of the test head holder 17. This is accomplished by using a third positioning motor 44 mounted on a base plate 43 of the slide 27 having the rolls 28. The shaft 45 of the motor 44 is perpendicular to the plane of the longitudinal motion of the slide 27 an extends through the base plate 43. A first sleeve 46 is arranged on the shaft 45 and is centered and secured against rotation and shifting by a pin 47. The sleeve 46 has a through hole 48 in the lower part which extends beyond the shaft 45.

A second sleeve 49 made of insulating material, e.g. polyamide, is pushed with a sliding fit onto the sleeve 46. The second sleeve 49 has a hole 50 on one side which corresponds to the through hole 48 in the sleeve 46. At the same height opposite hole 50 on the second sleeve, a longitudinal slot 51 is provided. The slot 51 does not extend over the entire height of the sleeve 49. A pin 52 is pushed through hole 50 and into through hole 48. The pin 52 extends into the longitudinal slot 51. The end of the pin 52 is provided with flats 53. Pin 52 therefore secures the two sleeves 46 and 49 against rotation without preventing their mutual motion in the axial direction over the length of the longitudinal slot 51. The upper limiting surface 54 of the longitudinal slot 51 and pin 52 serve as a stop to prevent the sleeve 49 from turning off sleeve 46.

The longitudinal motion of the two sleeves 46, 49 relative to each other is controlled by providing an external threading 55 on the insulating sleeve 49. A setting nut 56 is screwed onto the external threading 55 and is axially secured by a snap ring 57 while remaining rotatable. The setting nut 56 is only threaded 58 over a certain part of its inside circumference. By rotating the setting nut 56, which does not shift in the axial longitudinal direction, the insulating sleeve 49 is moved in the longitudinal direction relative to the sleeve 46.

The lower end of the sleeve 49 has a flange 59 including a centering rim 60. The centering rim 60 centers the cup-like test head holder 17 held at the flange 59 by means of a screw cap 61. A pin 62 protects against rotation between the sleeve 59 and the test head holder 17. All of the connecting parts between the shaft 45 and the third positioning motor 44 and test head holder 17 are therefore secured against rotation.

The cup-like test head holder 17 terminates with a holding ring 63 on the end facing the end face 2 of the test shaft 1. The holding ring 63 surrounds the test head 4 and an ancillary wedge 9. Several pins 64 protect against rotation between the holding ring 63 and the test head holder 17. The holding ring 63 is additionally braced with springs 65 against the upper end face wall 66 of the test head holder 17. The springs 65 generate a certain amount of contact pressure from the test head 4 and the ancillary wedge 9 onto the end face 2 of the test shaft 1. The test head 4 adjusts itself at an angle according to the inclination of the ancillary wedge 9 when placed on the end face 2. This allows the ultrasound pulses emitted by the test head 4 to sonicate the est shaft at an angle through the shaft's end face 2.

The test head holder 17 has a lateral opening 67 through which the feeding cable 68 for the test head 4 is coupled. In addition, one of the rotation protecting pins 64 between the holding ring 63 and the test head 17 is provided with a hole 69. The hole 69 allows the coupling means, required for carrying out the ultrasound pulse echo method, into the interior of the test head holder 17. The coupling means is then conducted via the holes 70 to the coupling surface of the ancillary wedge 9 on the end face 2 of the test shaft 1.

The specific mechanical design of the slide parts, including the third positioning motor 44, provides the third degree of freedom for the adjustable mechanical device 3, namely, rotation of the test head 4 about the axis of the test head holder 17 coinciding with the axis of the shaft 45 of the third positioning motor 44. Because of the rotation, the test head 4 is tilted according to the inclination of the ancillary wedge 9. Therefore, the sonicating ultrasound beam is displaced along the conical surface of a cone.

Because the fastening of the test head holder 17 relative to the positioning motor's shaft 45 is longitudinally minimal, simple matching of the test head position to the geometric conditions of the test shaft's end face are achieved. This additionally allows the test head 4 to be coupled in slot areas. Further, for any desired inclined positions of the test head 4, the springs 65 guarantee sufficient contact pressure in the interior of the test head holder 17. Additionally, the holding device has the advantage of using an insulating second sleeve 49 such that electrical and magnetic insulation of the test head 4 relative to the adjustable mechanical device 3 is achieved. Therefore, external disturbing influences which otherwise would obscure small echo pulses are kept from the test head 4. This has the advantage of allowing small incipient cracks to be detected.

What is claimed is:

1. An ultrasound pulse echo method for detecting cracks in a shaft using a test head coupled to an end face of the shaft, which emits a series of ultrasound pulses of a given frequency and receives a series of reflected sound echoes in a sound receiver contained in the test head and recorded by an evaluation device, the method comprising the steps of:
    (a) placing the test head on the end face of the shaft at a radial distance from a central axis of the shaft via an adjustable mechanical device coupled to said shaft;
    (b) delivering sound pulses having a high frequency in the range of 4 to 8 MHz from the test head for conducting measurements; and
    (c) displacing the test head in the course of the measurements at least over part of the circumference of a circle defined by the radial distance of the test head from the central axis.

2. A method according to claim 1 further comprising the steps:
    (d) coupling an ancillary wedge to the test head through a test head holder; and
    (e) rotating the test head about an axis of the test head holder.

3. A method according to claim 1 wherein the step of placing the test head on the end face of the shaft at a radial distance from the central axis of the shaft further comprises the step of adjustably selecting the radial distance from the central axis of the shaft with the adjustable mechanical device.

4. A method according to claim 1 further comprising the step of displacing the test head along the radius from the central axis of the shaft, said displacing along the radius and the circumference being carried out independently of each other.

5. A method according to claim 1 further comprising the step of releasing the motions of the test head by a plurality of positioning motors coupled to the adjustable mechanical device centered on the central axis of the shaft.

6. A method according to claim 5 further comprising the step of receiving coupling screws for the mechanical device in a plurality of holes provided on the end face of the shaft to serve as a coupling flange for the adjustable mechanical device.

7. A method according to claim 1 wherein the shaft is a turbine shaft coupled to a generator and the test head, in an installed condition, is placed on the generator side end face of the turbine shaft.

8. An ultrasound pulse echo apparatus for detecting cracks in a shaft, comprising:
    (a) a test head;
    (b) a test head holder containing said test head;
    (c) an ancillary wedge coupled to said test head holder and abutting said test head;
    (d) means to cause said test head to emit a series of ultrasound pulses of a given frequency and receive a series of reflected sound echos in a sound receiver contained in the test head;
    (e) an evaluation device for recording the received sound echos;
    (f) a support body;
    (g) means for coupling the support body to the shaft, said coupling means being adjustable;
    (h) a guide ring coupled to said support body;
    (i) a second ring centrally supported by and within said guide ring, said second ring supported for rotation with respect to said guide ring;

(j) two tracks coupled to said second ring and located parallel to each other at the same distance from the center of said rings; and (k) a slide assembly longitudinally movable on said tracks, said slide assembly supporting said test head holder.

9. An apparatus according to claim 8 further comprising at least two traverses for fastening the tracks to the second ring.

10. An apparatus according to claim 8 further comprising a first positioning motor rigidly coupled to the support body for moving the slide on the tracks.

11. An apparatus according to claim 10 further comprising:

(a) a drum driven by said first positioning motor;

(b) a guide track connected to said slide, the length of said guide track corresponding at least to the desired longitudinal motion of the slide; and (c) a band fastened to said drum, said band being wound and unwound around said drum, and having ends fixed on the guide track.

12. An apparatus according to claim 11 wherein the band is comprised of sheet metal in the form of a tuning fork having two outer ends and a central part, said outer ends are fixed to the guide track and said central part is fixed to the drum.

13. An apparatus according to claim 11 further comprising a means for tightening the band.

14. An apparatus according to claim 8 wherein the second ring has an external gearing, the apparatus further comprising:

(a) a second positioning motor; and (b) a pinion coupled to said second positioning motor, said second motor is fastened on the support body for the guide ring and said pinion is in engagement with the external gearing.

15. An apparatus according to claim 14 further comprising means for radially displacing the pinion of the second positioning motor relative to the external gearing of the second ring.

16. An apparatus according to claim 15 wherein the means for radially displacing comprises:

(a) a base plate coupled to the second positioning motor;

(b) a support shoe fastened to the support body of the guide ring and on which the base plate slides;

(c) a screw fixed in the support shoe; and (d) a knurled nut coupled to said screw, said knurled nut releasing the radial displacement of said pinion.

17. An apparatus according to claim 8 wherein the slide assembly on the side opposite the test head and test head holder further comprises:

(a) a third positioning motor coupled to said slide assembly; and (b) a shaft coupled to said third positioning motor extending through the slide, said test head being centered via the test head holder and fastened on the shaft, said test head is further secured against rotation.

18. An apparatus according to claim 17 wherein the test head holder is fastened to the shaft of the third positioning motor in an electrically insulating manner.

19. An apparatus according to claim 17 wherein the fastening of the test head holder on the shaft of the third positioning motor further comprises two sleeves pushed on each other and centrally ligned, said sleeves are movable relative to each other in the longitudinal direction, one of said sleeves is rigidly connected to the shaft of the third positioning motor and the other of said sleeves centers and supports the test head holder.

20. An apparatus according to claim 19 wherein the sleeve supporting the test head holder has external gearing onto which a setting nut is screwed.

21. An apparatus according to claim 18 wherein the sleeve supporting the test head holder is made of an insulating material and contains a longitudinal slot, the apparatus further comprises an anti-rotation device received in said slot to prevent rotation between said sleeves, the boundary surface of said slot forming a stop for the anti-rotation device.

22. An apparatus according to claim 18 wherein the connection between the shaft and the test head holder is secured against rotation.

23. An apparatus according to claim 18 wherein the test holder has a hole for supplying a means for coupling with the contact area of the test head and the ancillary wedge.

* * * * *